United States Patent [19]

Bertelli

[11] Patent Number: 4,684,520

[45] Date of Patent: Aug. 4, 1987

[54] PHARMACEUTICAL COMPOSITIONS HAVING CEREBRAL ANTIANOXIC AND METABOLIC ACTIVITIES

[75] Inventor: Alberto Bertelli, Milan, Italy

[73] Assignee: Seuref A.G., Vaduz, Liechtenstein

[21] Appl. No.: 718,884

[22] Filed: Apr. 2, 1985

[30] Foreign Application Priority Data

Apr. 9, 1984 [CH] Switzerland .................. 1774/84

[51] Int. Cl.$^4$ .................. A61K 37/48; A61K 31/685
[52] U.S. Cl. .................. 424/94.10; 514/78; 514/824; 514/907
[58] Field of Search .................. 424/94; 514/78

[56] References Cited

U.S. PATENT DOCUMENTS 4,073,883  2/1978  Yasuda et al. .................. 424/94
4,221,784  9/1980  Growdon et al. .................. 514/78

FOREIGN PATENT DOCUMENTS 0083108  7/1983  European Pat. Off. .......... 514/78
0056315  5/1978  Japan .................. 514/78
0042616  3/1982  Japan .................. 424/94
0075916  5/1982  Japan .................. 514/78
0142911  9/1982  Japan .................. 424/94
0649917  6/1985  Switzerland .................. 424/94

OTHER PUBLICATIONS

Merck Index 9th ed., p. 1263, No. 9496, 1976.
Chem. Abst. 73: 107444g, 1970.

*Primary Examiner*—Johnnie R. Brown
*Assistant Examiner*—John W. Rollins
*Attorney, Agent, or Firm*—Bucknam and Archer

[57] ABSTRACT

The invention relates to novel pharmaceutical compositions containing ubiquinone, particularly Coenzyme $Q_{10}$, and mixtures of phospholipids having organic or vegetal origin, in weight-ratios ranging from 1/1 to 1/100,000, together with pharmaceutically acceptable excipients.

The pharmaceutical compositions of the invention are useful in the treatment of pathological conditions related to insufficient cerebral perfusion, atherosclerosis or enzymatic impairments involving cerebral metabolic deficiencies, and generally in conditions deriving from cerebral and tissular postanoxy.

Said pharmaceutical composition allows a better absorption of Coenzyme $Q_{10}$.

4 Claims, No Drawings

PHARMACEUTICAL COMPOSITIONS HAVING CEREBRAL ANTIANOXIC AND METABOLIC ACTIVITIES

The present invention relates to novel pharmaceutical compositions containing a ubiquinonic coenzyme together with one or more phospholipids, which are of known importance in the metabolism and biochemistry of tissues, particularly at the cerebral level.

The compositions according to the invention contain, as the active ingredient, a ubiquinonic coenzyme and phospholipids of animal (particularly from cerebral and nervous tissues), vegetal, synthetic or semisynthetic origin.

A particularly preferred ubiquinonic coenzyme is ubiquinone $Q_{10}$ (2,3-dimethoxy-5-methyl-6-decaprenyl-benzoquinone).

Preferred phospholipids are those selected from the group consisting of phosphatidylcholine phosphatidylserine, phosphatidylethanolamine, phosphatidylinositole, phosphatidic acid, diphosphoinositide, lysolecithin, dipalmitylphosphatidylcholine, cytidindiphosphocholine, cholineglycerophospholipid, lysocephaline, phosphonolipids, phosphatidylglycerol and glycerophospholipids, or similar compounds, such as lecthin and its derviatives.

The compositions of the invention contain the ubiquinonic coenzyme and the phospholipids in ratios ranging from 1 to 100,000, preferably from 10 to 1000.

The compositions according to the present invention exhibit an effective therapeutic action in the prevention and treatment of pathological conditions related to cerebral enzymatic and metabolic impairments, such as atherosclerosis, fatigability, loss of memory, neuroendocrine diseases and generally in the conditions deriving from cerebral and tissular postanoxy.

Coenzyme $Q_{10}$ has a structure consisting of a guinone ring and a side chain having ten isoprenoid units which make it liposoluble and suitable for settling in the mitochondrial membrane, wherein it acts as an electron carrier (Morton, R. A.—Nature 182-1764-1958; Gale P. et al.—Arch. Biochem. Biophys. 93-211-1961).

Since tissular and cellular energetic processes are related to the hydrogenionic transport, a defect or lack of this enzymatic system may also involve serious metabolic diseases.

In fact, a relation has been found between deficiencies in the Coenzyme $Q_{10}$ content in the myocardiac, muscular, gingival and cerebral tissues and such specific pathological conditions as myocardiac insufficiency, muscular dystrophy, periodontitis and nervous disorders (Folkers K., Littarru G. P., Ho L., Runge T. M., Cooley D.—Int. J. Vit. Res. 40-380-1970).

Exogenous administration of Coenzyme $Q_{10}$ caused the remission of a great part of the symptomatology of said pathological conditions (Yamasawa J.—Biomedical and Clinical Aspects of Coenzyme Q—Elsevier—North Holland Ed. Vol. 2—pag. 333-1980; Nyler W. G.—Idem, pag. 349-1980; Wilkinson E. G., Arnold R. M.—Res. Comm. Chem. Path. Pharmacol. 12-111-1975; Gamadak et al.—Biomedical and Clinical Aspects of Coenzyme Q—Elsevier—North Holland Ed. Vol. 2—pag. 123-1980).

The fact that ubiquinone is present not only in the mitochondries, but also in other membranes, such as Golgi apparatus membranes, endoplasmatic reticulum membranes, as well as in plasmatic membranes, proves that Coenzyme $Q_{10}$ plays a role substantially more important and extensive than that hitherto described.

All the patterns of tissular suffering both of anoxic kind and of energy lack conditions, as well as suffering caused by free radicals production, may be controlled by means of ubiquinone.

By administering ubiquinone, in fact, a depressed mitochondrial respiration may be restored, ATP cellular concentration may be increased, phospholipases action may be blocked and the cellular membrane may be maintained integer.

The integrity and functionality of cellular membranes is also regulated, especially at cerebral level, by the phospholipid synthesis and the associated energetic systems, which are related to ATP.

The liposolubility of Coenzyme $Q_{10}$ is another factor which allows the biochemical action of Coenzyme $Q_{10}$ at the level of cellular and subcellular phospholipidic component (White D. A.—Form and Function of Phospholipids—Ansell G. B. et al. Ed.—Elsevier Pub. Amsterdam—pag. 441-1973; Young D. L., Powell G., McMillan W. O.—J. Lipid. Res. 12-1-1971; Soto E. F. et al.—Arch. Biochem. Biophys. 150-362-1972; Krawiek L. et al.—Acta Physiol. Latino-americana 25-439-1975).

This fact, together with the ascertainment that the administration of exogenous phospholipids may increase and induce their incorporation and biosynthesis at the cerebral and nervous tissular level, allows to understand how important is the presence, together with the phospholipidic fraction to be administered, of a system for the energetic transport which can provide for the phospholipid biosynthesis and the cellular phospholipidic incorporation directly in the sites wherein said transformations occur (Porcellati G.—Central Nervous System. Studies on Metabolic Regulation and Function—Gennazzani G.—Ed. Springer Pub. Berlin 1974).

It has now surprisingly been found that the pharmaceutical compositions of the invention display remarkable therapeutic effects by virtue of unforeseeable synergistic interactions between the ubiquinonic component and the phospholipids.

The validity of the present invention is in no way based on the verification of the above mentioned biological mechanism.

The lipidic and/or phospholipidic components are also able to make the ubiquinone component soluble, thus allowing the parenteral administration. The ubiquinone compound exerts an anti-oxidizing action on the phospholipids.

The results of toxicological and pharmacological tests carried out on the present compositions are reported below.

TOXICOLOGY

The toxicological tests were carried out by combining Coenzyme $Q_{10}$ either with a phospholipidic mixture consisting of phosphatidylcholine, phosphatidylethanolamine+phosphatidylserine, sphingomyelin, phosphatidylinositol in a 40/34/10/16 percent ratio, respectively, or with soy lecithin.

The different formulations were administered orally and parenterally, in Wistar rats and in Swiss mice of both sexes.

$DL_{50}$ of the product could not be determined, due to the known very low toxicity of the components of the association.

The oral administration of 1 g/kg of Coenzyme $Q_{10}$ together with 0.5-1 g or 2 g of phospholipid mixture as well as soy lecithin, did not cause any detectable toxic effect.

Also the parenteral administration proved to be well tolerated: the administration by the intraperitoneal route of an association containing 300 mg/kg of Coenzyme $Q_{10}$ and 0.5 g or 1 g/kg of phospholipid mixture, did not cause deceases or toxic effects.

The compositions of the invention proved to be well tolerated also as far as the chronic toxicity is concerned.

The oral administration during 3 months of a mixture of 100 mg of Coenzyme $Q_{10}$ and 500 mg of phospholipids or 2 g of soy lecithin, in Wistar rats and Beagle dogs (of both sexes) did not cause detectable changes in growth, survival or biologic parameters related to blood and haematochemistry.

PHARMACOLOGY

Pharmacological tests (a) Test on the experimental cerebral anoxia

Male New Zealand rabbits were employed, which were placed in a close cage, impermeable to the air. Then, the air was removed from the cage and substituted with nitrogen. The gradual substitution of air by nitrogen induced an anoxic condition detected by electroencephalographic changements progressing up to the electrical silence.

The administration of Coenzyme $Q_{10}$ (50 mg/kg by the intraperitoneal route or 200 mg/kg by the oral route) may result in a decrease of the anoxic state, which decrease may be detected by measuring the times necessary for the onset of anoxia symptoms and the times necessary for the recovery of normal electroencephalogram: they show to be respectively substantially prolonged and reduced if, before the beginning of the experiment, Coenzyme $Q_{10}$ is orally administered together with 1 g/kg of a mixture of phospholipids (phosphatidylcholine, phosphatidylethanolamine, phosphatidylserine, sphingomyelin, phosphatidylinositol) or 1 g/kg of soy lecithin. The same increase in the antianoxic activity of Coenzyme $Q_{10}$ may be obtained by intraperitoneal administration of 100 mg/kg of phospholipids or soy lecithin.

The phospholipid mixture as well as soy lecithin show no effect in the above described anoxia test, if administered by oral or intraperitoneal route without Coenzyme $Q_{10}$.

All this proves the substantial increase on the Coenzyme $Q_{10}$ antianoxic activity displayed by the phospholipids mixture or, in less extent, by soy lecithin.

The results are reported in the following Table 1.

TABLE I

Cerebral antianoxic activity: cerebral resistance and recovery time.

| Treatment | g/kg | Administration route | Cerebral resistance[1] | Recovery time[2] |
|---|---|---|---|---|
| Controls | — | — | 30'11" | 29'50" |
| Phospholipid mixture | 1 | oral | 31'55" | 29'10" |
| Soy lecithin | 1 | oral | 30'25" | 30'55" |
| Coenzyme $Q_{10}$ | 0.200 | oral | 33'10" | 24'30" |
| Phospholipid mixture + Coenzyme $Q_{10}$ | 1 0.200 | oral oral | 38'40" | 16'22" |
| Soy lecithin + | 1 | oral | 36'28" | 17'40" |

TABLE I-continued

Cerebral antianoxic activity: cerebral resistance and recovery time.

| Treatment | g/kg | Administration route | Cerebral resistance[1] | Recovery time[2] |
|---|---|---|---|---|
| Coenzyme $Q_{10}$ | 0.200 | oral | | |

[1]Time necessary for first appearance of electroencephalographic changes.
[2]Time necessary for restoration of normal electroencephalogram after return of air exposition.

Another test used to evaluate the cerebral antianoxic action of Coenzyme $Q_{10}$ was that of observing its effect on ATP content in anoxic cerebral tissue after different times from the decapitation of albino mice (Swiss Albino Mice) of the mean weight of 20 grams.

Two or four hours before the decapitation, the animals were treated with Coenzyme $Q_{10}$ alone or in combination with phospholipids or soy lecithin. The evaluation of the ATP content was carried out after 30, 60 and 120 minutes from the decapitation.

The ATP dosage was performed by HPLC. After the decapitation, the cerebral tissue was homogenized at low temperature in neutralized perchloric acid (6%) and after 30 minutes the KOH treated surnatant was subjected to HPLC analysis using as the mobile phase 0.5M $NH_4H_2PO_4$.

The protein content of the precipitate after perchloric acid treatment was dissolved in NaOH and determined by the biuret reaction.

As shown by the data exposed in the Table II, the Coenzyme $Q_{10}$ treatment slightly increases the ATP content in the anoxic brain but this increase becomes surprisingly evident in the mice treated with Coenzyme $Q_{10}$ plus phospholipids or soy lecithin which are themself inactive.

It is therefore confirmed an unexpected antianoxic synergistic effect of the composition according to the invention.

The maximum ATP increase in anoxic brain can be observed after 60" from the decapitation with a value which is about 200% higher in comparison to the controls in mice treated with Coenzyme $Q_{10}$ together with the phospholipid mixture.

TABLE II

| | ATP content in mouse brain (nmol/mg prot) | | |
|---|---|---|---|
| | TIME AFTER DECAPITATION | | |
| TREATMENT | 30' | 60' | 120' |
| Controls | 5.5 | 2.8 | 1.8 |
| Coenzyme $Q_{10}$ | 6.5 | 4.8 | 2.2 |
| Phospholipids | 5.7 | 4.4 | 2.0 |
| Soy lecithin | 5.4 | 4.2 | 1.9 |
| Coenzyme $Q_{10}$ + phospholipid mixture | 7.5 | 8.2 | 3.3 |
| Coenzyme $Q_{10}$ + soy lecithin | 7.1 | 7.3 | 2.9 |

Test on radio-labelled phosphate[(32P)] incorporation in the cerebral ATP, in organic phosphates and in brain phospholipids in animals subjected to cerebral anoxia These tests were carried out in the rat administering by the oral route the soy lecithin phospholipids mixture or Coenzyme $Q_{10}$, alone or combined together according to the new pharmaceutical composition.

One hour after the administration, the animals (5 rats per group) were placed in a suitable cage wherein the air was rapidly substituted by pure nitrogen.

After about 12 minutes of ipoxia, the animals showed pre-coma symptoms. At that moment, the animals were exposed again to free air and were injected with radio-labelled phosphorus($^{32P}$).

After 60 minutes the incorporation of 32P in the cerebral ATP, in cerebral organic phosphates and in cerebral phospholipids was calculated.

The results reported in Table III show a marked increase, in comparison with the non treated animals, of the 32P incorporation in cerebral ATP as well as in organic phosphates and in cerebral phospholipids, in the animals treated with the combination according to the invention, even if in a lower extent than with soy lecithin.

This fact shows a restoration of the energy producing systems related to the nervous cerebral function, said restoration being surprisingly significant and not ascertainable, on the contrary, with the single components.

Also these tests show the marked synergism which is unexpectedly found at the level of the systems regulating the energy production and the function of the cerebral tissues, when these are damaged by anoxia, using the combination of Coenzyme $Q_{10}$ and a phospholipid mixture or soy lecithin according to the invention.

TABLE III

| Treatment | g/kg | Administration route | Incorporation of 32P in ATP % dose 32P/g brain | Incorporation of 32P in organic phosphate % dose 32P/g brain | Incorporation of 32P in phospholipids % dose 32P/g brain |
| --- | --- | --- | --- | --- | --- |
| Antianoxic cerebral activity. Incorporation of 32P in cerebral ATP, organic phosphates and phospholipids. | | | | | |
| Controls | — | — | $50.10^{-4}$ | $120.10^{-4}$ | $30.10^{-4}$ |
| Phospholipid mixture | 1 | oral | $40.10^{-4}$ | $140.10^{-4}$ | $25.10^{-4}$ |
| Soy lecithin | 1 | oral | $50.10^{-4}$ | $130.10^{-4}$ | $25.10^{-4}$ |
| Coenzyme $Q_{10}$ | 0.200 | oral | $60.10^{-4}$ | $160.10^{-4}$ | $30.10^{-4}$ |
| Phospholipid mixture + Coenzyme $Q_{10}$ | 1 0.200 | oral oral | $90.10^{-4}$ | $250.10^{-4}$ | $70.10^{-4}$ |
| Soy lecithin + Coenzyme $Q_{10}$ | 1 0.200 | oral oral | $80.10^{-4}$ | $230.10^{-4}$ | $60.10^{-4}$ |

(b) Test on the protective activity on experimental atherosclerotic lesions

Also this test shows the clear synergism between Coenzyme $Q_{10}$, phospholipids or soy lecithin.

In fact, the combination of Coenzyme $Q_{10}$ and a mixture of phospholipids (phosphatidylcholine, phosphatidilethanolamine, sphyngomieline, phosphatidylserine, phosphatidylinositol) or soy lecithin (Coenzyme $Q_{10}$ 50 mg/kg o+phospholipid mixture 500 mg/kg or soy lecithin 500 mg/kg, by oral route) inhibit the formation of atherosclerotic lesions in a substantially more effective way, than the administration of Coenzyme $Q_{10}$ alone or phospholipids or soy lecithin alone.

In the test, atherosclerotic lesions were induced in the rat by means of an atherogenic diet: casein 24%, cotton oil 10%, salt 5%, sugar 61%, cholesterol 0.5%, $D_2$ vitamin 200 m UST/g of diet.

This diet was administered during 6 weeks to rats treated respectively with Coenzyme $Q_{10}$ alone or phospholipids or lecithin alone, or Coenzyme $Q_{10}$ together with phospholipids or lecithin, and to control animals. After 6 weeks all the animals were killed and examined. It was noticed that while the control rats as well as the rats treated with Coenzyme $Q_{10}$ alone or phospholipids or soy lecithin alone had serious atherosclerotic lesions at the aortic and myocardial level, the rats treated with Coenzyme $Q_{10}$ and phospholipids or lecithin, showed no or negligible atherosclerotic lesions.

From the above, the advantageous and surprising synergic properties, which can be obtained combining the specified active principle, are evident.

The pharmaceutical compositions according to the invention may be formulated in form of capsules, tablets, dragees, lozenges, granulates, syrups or parenteral solutions, in admixture with suitable excipients.

Some illustrative non limiting examples of said compositions are given hereinbelow:

capsules, containing 10 mg of Coenzyme $Q_{10}$ and 0.5 of phospholipids;

capsules, containing 100 mg of Coenzyme $Q_{10}$ and 0.5 g of phospholipids;

granulates, containing 10 mg of Coenzyme $Q_{10}$/100 g of soy lecithin;

vials, containing 10 mg of Coenzyme $Q_{10}$, 500 mg of soybean oil and 50 mg of phospholipids from yolk;

vials, containing 300 mg of phospholipids (40% phosphatidylcholine, 35% phosphatidylethanolamine and phosphatidylserine, 10% sphingomyelin and 15% other phospholipids) and 10 mg of Coenzyme $Q_{10}$.

I claim:

1. A pharmaceutical composition for exhibiting cerebral antianoxic activity consisting of component (a) which is Coenzyme $Q_{10}$ and component (b) which is a mixture of phosphatidylcholine, phosphatidylserine, phosphatidylethanolamine, phosphatidylinositol and sphingomyelin or soy lecithin in a 1:5 ratio of said component (a) to component (b) and excipients.

2. The composition according to claim 1 in form of capsules, dragees, tablets, granulates.

3. A method of treatment of anoxia which consists of administering to a subject affected by anoxia an effective amount of a composition which consists of component (a) which is Coenzyme $Q_{10}$ and component (b) which is a mixture of phosphatidylcholine, phosphatidylserine, phosphatidylethanolamine, phosphatidylinositol and sphingomyelin or soy lecithin in a 1:5 ratio of said component (a) to component (b) and excipients.

4. The method according to claim 3 wherein said composition is administered orally.

* * * * *